United States Patent [19]
Kanegae et al.

[11] Patent Number: 5,599,697
[45] Date of Patent: Feb. 4, 1997

[54] METHOD OF PRODUCING β-1,3-GLUCAN

[75] Inventors: Yukihiro Kanegae, Kobe; Kazutsugu Kimura, Harima-cho; Isamu Nakatsui, Kobe, all of Japan

[73] Assignee: Takeda Chemical Industries, Ltd., Osaka, Japan

[21] Appl. No.: 465,184

[22] Filed: Jun. 5, 1995

Related U.S. Application Data

[63] Continuation of Ser. No. 165,497, Dec. 13, 1993, abandoned.

[30] Foreign Application Priority Data

Dec. 14, 1992 [JP] Japan ................... 4-333257
Jul. 5, 1993 [JP] Japan ................... 5-165792
Jul. 9, 1993 [JP] Japan ................... 5-170619

[51] Int. Cl.⁶ ........................... C12P 19/04; C12P 19/08
[52] U.S. Cl. .................... 435/101; 435/103; 435/829; 536/123.12; 536/124
[58] Field of Search ................ 435/101, 103, 435/829; 536/123.12, 124

[56] References Cited

U.S. PATENT DOCUMENTS 3,754,925  8/1973  Kimura et al. ..................... 99/1
4,355,106  10/1982  Lawford ........................... 435/101

FOREIGN PATENT DOCUMENTS 0322393  6/1989  European Pat. Off. .
0515216  11/1992  European Pat. Off. .
60/58064  4/1985  Japan .

OTHER PUBLICATIONS

"Agricultural Biological Chemistry, Growth and β–Glucan 10C3K Production by a Mutant of *Alcaligenes faecalis var. myxogenes* in Defined Medium" Harada et al., vol. 30, No. 8, pp. 764–769, 1966.

Primary Examiner—John W. Rollins
Assistant Examiner—Francisco C. Prats
Attorney, Agent, or Firm—Wenderoth, Lind & Ponack

[57] ABSTRACT

The present invention comprises a method of producing β-1,3-glucan wherein a microbe capable of producing β-1,3-glucan is cultured in a medium containing as a nitrogen source an ammonium salt of an organic carboxylic acid the microbe can assimilate wherein the β-1,3-glucan is produced and accumulated, and then harvesting. The β-1,3-glucan production method of the present invention does not require addition of a pH regulator such as calcium carbonate or alkali ions, since the medium does not decrease in pH because a microbe capable of producing β-1,3-glucan is cultured in a medium containing as a nitrogen source an ammonium salt of an organic carboxylic acid which the microbe can assimilate. For this reason, cultivation is not adversely affected, nor does any salt form in the medium, aspects which facilitate purification of said glucan, offering an industrially excellent production method. Moreover, the method of the present invention makes it feasible to produce β-1,3-glucan at high productivity and high yield relative to sugar.

10 Claims, No Drawings

METHOD OF PRODUCING β-1,3-GLUCAN

This application is a continuation of now abandoned application Ser. No. 08/165,497, filed Dec. 13, 1993.

FIELD OF THE INVENTION

The present invention relates to a method of producing β-1,3-glucan.

BACKGROUND OF THE INVENTION

There are various naturally-occurring microbes which produce β-1,3-glucan. For example, microbes such as those belonging to the genus Alcaligenes or Agrobacterium are known to extracellularly produce a β-1,3glucan known as curdlan [New Food Industry, Vol. 20, p. 49 (1978), U.S. Pat. No. 3,754,925 etc.], and microbes such as those belonging to the genus *Euglena* are known to produce a β-1,3-gl etc.).

Conventional production methods for β-1,3-glucan based on cultivation of such microbes use as nitrogen sources various inorganic salts such as ammonium phosphate, ammonium sulfate and ammonium hydrochloride, urea, asparagine etc. [Agricultural Biological Chemistry, Vol. 30, pp. 764–769 (1966), U.S. Pat. No. 3,754,925, JP-A 60-58064 etc.]. When these inorganic salts are used, the pH of the medium is maintained at a prescribed level by means of pH regulation such as by addition of calcium carbonate to the medium or by addition of alkali ions such as those of caustic soda to the medium while monitoring the pH, since pH decreases during cultivation.

Conventional methods are known to pose problems such as the formation of sparingly soluble salts resulting from the reaction of the calcium carbonate added to the medium with an union such as the phosphate, sulfate or hydrochloride ion in a compound added as a nitrogen source. Another problem is the adverse effect of the alkali ion added for pH regulation on cultivation. In addition, if salts form in the culture broth, an additional operation or step is required to remove them in a purification process. All these phenomena are undesirable.

OBJECTS OF THE INVENTION

The main object of the present invention is to provide a method of a β-1,3-glucan using no inorganic salt as a nitrogen source.

This object as well as other objects and advantages of the present invention will become apparent to those skilled in the art from the following description.

SUMMARY OF THE INVENTION

The present invention relates to a method of producing β-1,3-glucan with high productivity and high yield relative to sugar without forming a salt during cultivation.

According to the present invention, there is provided:
1) A method of producing β-1,3-glucan which comprises culturing a microbe capable of producing β-1,3-glucan in a medium containing as a nitrogen source an ammonium salt of an organic carboxylic acid which the microbe can assimilate wherein the β-1,3-glucan is produced and accumulated, and then harvesting the β-1,3-glucan,
2) The method of the above paragraph 1, wherein the organic carboxylic acid is a mono- to tri-carboxylic acid having 3 to 6 carbon atoms,
3) The method of the above paragraph 1, wherein the organic carboxylic acid is an organic carboxylic acid which forms the citric acid cycle,
4) The method of the above paragraph 1, wherein the organic carboxylic acid is an acidic amino acid,
5) The method of the above paragraph 1, wherein the organic carboxylic acid is selected from the group consisting of succinic acid, fumaric acid, α-ketoglutaric acid and lactic acid,
6) The method of the above paragraph 1, wherein the organic carboxylic acid is succinic acid,
7) The method of the above paragraph 1, wherein the amount of the organic carboxylic acid is about 0.5 to about 20 g/l,
8) The method of the above paragraph 1, wherein the ammonium salt of organic carboxylic acid is used in an mount to reach a total N content of about 0.4 to about 3 g/l medium,
9) The method of the above paragraph 1, wherein the β-1,3-glucan is curdlan,
10) The method of the above paragraph 1, wherein the microbe belongs to the genus Agrobacterium or Alcaligenes,
11) A method of producing curdlan which comprises:
    culturing a microbe belonging to the genus Agrobacterium or Alcaligenes in a medium containing as a nitrogen source an ammonium salt of an organic carboxylic acid which the microbe can assimilate wherein the curdlan is produced and accumulated, the amount of the organic carboxylic acid being about 0.5 to about 20 g/l, the organic carboxylic acid being selected from an acid which forms the citric acid cycle; and then
    harvesting the curdlan,
12) A method of producing curdlan which comprises
    culturing a microbe belonging to the genus Agrobacterium or Alcaligenes in a medium containing as a nitrogen source an ammonium salt of an organic carboxylic acid which the microbe can assimilate wherein the curdlan is produced and accumulated, the amount of the organic carboxylic acid being about 0.5 to about 20 g/l, the organic carboxylic acid being an acidic amino acid; and then
    harvesting the curdlan, and
13) A method of producing β-1,3-glucan which comprises:
    culturing a microbe capable of producing β-1,3-glucan in a medium containing as a nitrogen source an ammonium salt of an organic carboxylic acid which the microbe can assimilate wherein the β-1,3-glucan is produced and accumulated, the organic carboxylic acid and the ammonium salt being separately added to the medium; and then
    harvesting the β-1,3-glucan.

DETAILED DESCRIPTION OF THE INVENTION

The β-1,3-glucan of the present invention is a polysaccharide consisting of glucose which are primarily bonded through β-1,3-glycosidic linkages. Specific examples thereof are curdlan, paramylon and the like. In this invention, curdlan is preferred.

Any microbe can be used for the present invention, as long as it is capable of producing β-1,3-glucan. Such microbes include those belonging to the genus Alcaligenes or Agrobacterium when the β-1,3-glucan is curdlan. Specifically, microbes belonging to the genus Alcaligenes include *Alcaligenes faecalis var. myxogenes* 10C3K [Agricultural Biological Chemistry, Vol. 30, p. 196 (1966)] and *Alcaligenes faecalis var. myxogenes* 10C3K mutant NTK-u (IFO 13140) (JP-B 48-32673, U.S. Pat. No. 3,754,925) and the like. Microbes belonging to the genus Agrobacterium include *Agrobacterium radiobacter* (IFO 13127) and its mutant U-19 (IFO 13126) (JP-B 48-32674). *Alcaligenes faecalis var. mixogenes* 10C3 (IFO 13714) is described as *Agrobacterium sp. biovar* I (IFO 13714) in IFO Research Communications, Vol. 15, pp. 57–75 (1991) and the List of Cultures, 9th edition (1992), published by the IFO.

When the desired β-1,3-glucan is paramylon, usable microbes include those belonging to the genus Euglena. Specifically, such microbes include *Euglena gracilis* Klebs NIES-47, *Euglena gracilis* Klebs NIES-48 and *Euglena gracilis var. bacillaris pringsheim* NIES-49. These strains are known strains deposited at the Global Environment Forum (foundation, 16-2, Onogawa, Tsukuba-shi, Ibaraki, Japan).

Any organic carboxylic acid can be used in the ammonium salt of organic carboxylic acid as a nitrogen source for the present invention, as long as it can be assimilated by the microbe capable of producing β-1,3-glucan. Acidic organic carboxylic acids are preferred, more preferably mono- to tricarboxylic acids having 3 to 6 carbon atoms. Organic carboxylic acids which form the citric acid cycle and amino acids are still more preferred. The citric acid cycle (tricarboxylic acid cycle, Krebs cycle) is a cyclic sequence of reactions occuring in the living organism and forming a phase of the metabolic function in which acetic acid or acetyl equivalent is oxidized through a series of intermediate acids to carbon dioxide and water. Examples of the organic carboxylic acids which form the citric acid cycle are succinic acid, fumaric acid, α-ketoglutaric acid, citric acid, malic acid and the like. As the organic carboxylic acid, succinic acid, fumaric acid, α-ketoglutaric acid and lactic acid are preferred. Examples of the amino acids are glutamic acid, aspartic acid, alanine, proline, serine, threonine, histidine and the like. Acidic amino acids such as aspartic acid and glutamic acid are preferred.

The ammonium salt of organic carboxylic acid used in the present invention may be of any form, as long as it is capable of forming an ammonium salt in the medium, whether it is previously added to the medium in the form of an ammonium salt of organic carboxylic acid or whether an organic carboxylic acid and an ammonium salt are separately added to the medium. The method in which an organic carboxylic acid and an ammonium salt are separately added to the medium is preferred.

The organic carboxylic acid used in the present invention is used in an amount to reach a total N content of about 0.4 to about 3 g/l medium, preferably about 0.6 to about 1.8 g/l medium.

For example, when an organic carboxylic acid and an ammonium salt are separately added to the medium, the amount of organic carboxylic acid is chosen as appropriate for the microbe used, and preferably used to reach a total N content of about 0.4 to about 3 g/l medium. For example, when the desired β-1,3-glucan is curdlan, the mount of organic carboxylic acid used is preferably about 0.5 to about 20 g/l, more preferably about 1.5 to about 10 g/l. When the organic carboxylic acid is succinic acid, for example, its amount may be from about 2 to about 10 g/l, preferably about 2 to about 6 g/l.

The ammonium salt is preferably an inorganic ammonium salt or an aqueous solution thereof. Aqueous ammonia is preferred. When using aqueous ammonia, for instance, its amount may be chosen by calculation of its N content.

Addition of these substances to the medium may be achieved by various methods, such as one-time addition at initiation of cultivation and separate addition in portions during cultivation.

Urea and nitrates may be added to the medium, as long as the N content in the medium is retained within the above-described range for the present invention.

In addition to these medium components, other medium components for ordinary β-1,3-glucan culture are used. Examples of carbon sources include glucose, fructose, sucrose, crude sugar, molasses (e.g., beet molasses, sugar-cane molasses) and solutions of various starches (e.g., tapioca starch, sago starch, sweet potato starch, potato starch, corn starch) as saccharified. Examples of phosphorus sources include monopotassium phosphate, dipotassium phosphate, monosodium phosphate and disodium phosphate. These medium components may be used singly or in combination thereof as appropriate.

Sulfates, hydrochlorides, carbonates, phosphates and other salts of inorganic substances essential to microbial growth (e.g., calcium, potassium, magnesium, manganese, iron, zinc) and amino acids, vitamins and other substances essential to microbial growth may be optionally used singly or in combination. An antifoaming agent such as silicon oil and other additives may be added as necessary.

Although pH may not be regulated during cultivation, alkali and acid may be used to obtain preferable pH levels.

Cultivation temperature may be chosen as appropriate according to optimum growth temperature etc. for the microbe used; it is normally about 25° to about 35° C. Cultivation is continued until β-1,3-glucan production reaches maximum, cultivation time being normally about 40 to about 120 hours.

The β-1,3-glucan thus accumulated in the medium is harvested by a known means, (e.g. centrifugation, filtration, ultrafiltration etc.) and may be purified as necessary (e.g. U.S. Pat. No. 3,754,925 etc.).

The β-1,3-glucan obtained according to the present invention can be used in various fields such as the food, chemical and civil engineering industries.

The β-1,3-glucan of the present invention can be used as a thickening agent or a binder, for example, in foods. Subject foods include, but are not limited to, fish meat products (e.g., kamaboko, chikuwa, hampen, tempura, crab leg kamaboko, fish sausage), animal meat products (e.g., sausage, corned beef, loin ham, hamburgers, meat balls), cooked foods (e.g., gyoza, shaomai), noodles (e.g., raw/steamed/boiled Chinese noodles, udon noodles, instant noodles, buckwheat noodles, chow mein, gelatin noodles, rice noodles, macaroni, spaghetti, gyoza wrappings, shaomai wrappings), soybean products (e.g., tofu, frozen tofu, fried bean curd, vegetable-mixed fried bean curd), seasonings (e.g., miso, sauces, ketchup, sauces for Japanese foods), beverages, pastes (e.g., jam, marmalade, peanut butter, flour paste), bean jams, snacks, dairy products (e.g., butter, margarine, cheese, whipped cream), rice cakes and glutinous dumplings (e.g., bracken dumpling, sweet-sauced dumpling, rice cake covered with bean jam), cooked rice, confectionery (e.g., soy-seasoned rice crackers, candies, cookies, bean paste bars, Japanese raw cakes, fried cakes, Bavarian cream, moose, custard cream puff, marshmallow, chewing gum, ice cream, aspic jelly).

The β-1,3-glucan obtained by the present invention can be used as such or in combination with other food materials to yield various types of food, including konjak-like food, jellyfish-like food, various jellies, sheet-, somenand other forms of shaped food, jellied-fish-soup-like food, shaped cooked rice, edible films, low-calorie food and dietary fiber food.

In the chemical or civil engineering industries, for example, the β-1,3-glucan of the present invention can be used as a segregation reducing agent for a hydraulic composition such as concrete or mortar.

The β-1,3-glucan production method of the present invention does not require addition of a pH regulator such as calcium carbonate or alkali ions, since the medium does not decrease in pH because a microbe capable of producing β-1,3-glucan is cultured in a medium containing as a nitrogen source an ammonium salt of an organic carboxylic acid which the microbe can assimilate. For this reason, cultivation is not adversely affected, nor does any salt form in the medium, aspects which facilitate purification of said glucan, offering an industrially excellent production method.

Moreover, the method of the present invention makes it feasible to produce β-1,3-glucan at high productivity and high yield relative to sugar.

The present invention is hereinafter described in more detail by means of the following experimental examples and working examples. *Agrobacterium sp. biovar* I 10C3K, described in the following experimental examples and working examples, has been deposited under accession number IFO 15506 at the Institute for Fermentation, Osaka (foundation) since Jun. 9, 1993, and under accession number FERM BP-4357 at National Institute of Bioscience and Human-Technology, Agency of Industrial Science and Technology, Ministry of International Trade and Industry since Jul. 6, 1993.

EXPERIMENTAL EXAMPLE 1

One liter of the seed medium shown in Table 1 was prepared, adjusted to pH 7 and then dispensed to 200 ml conical flasks at 20 ml per flask. After each flask was autoclaved at 118° C. for 15 minutes, 1 loopful of a slant culture of *Agrobacterium sp. biovar* I (IFO 13714) was inoculated, followed by cultivation at 32° C. for 24 hours to yield a seed culture broth.

Separately, to the principal medium shown in Table 2 was added each ammonium salt listed in Table 3 as a nitrogen source to an N content of 0.64 g/l medium, and the medium adjusted to pH 7.5. The media containing respective nitrogen sources were each divided into two equal portions, to one of which calcium carbonate was added to a concentration of 0.3% (w/v).

Also prepared was a principal medium containing 2.0 g/l succinic acid and about 3.0 ml/l aqueous ammonia as nitrogen sources added to an N content of about 0.61 g/l medium (pH 7.5). This principal medium was divided into two equal portions, to both of which calcium carbonate was added to a concentration of 0.3% (w/v).

Each of the above media was dispensed in 200 ml conical flasks at 20 ml per flask and autoclaved at 118° C. for 15 minutes. Note that glucose was separately sterilized and a given amount was added before the seed medium was transferred.

To each principal medium was transferred 2 ml of the above-described seed culture broth, followed by cultivation at 32° C. for 96 hours.

To a 10 ml portion of this culture broth was added 50 ml of 1.0 N caustic soda, followed by stirring for about 1 hour to dissolve the curdlan formed in the culture broth. After cells were removed by centrifugation, the culture broth was diluted as appropriate and assayed for total sugar content by the phenolsulfuric acid method. Also determined was the residual glucose content in the culture supernatant, using a glucose assay kit (produced by Technikon). The residual glucose content was subtracted from the total sugar content, and the figure was multiplied by a factor of 0.9 to obtain the amount of curdlan produced.

Table 3 gives the amount of curdlan produced in each medium.

TABLE 1

| Seed Culture Medium Composition | |
|---|---|
| Component | (g/l) |
| Glucose | 10.0 |
| $(NH_4)_2HPO_4$ | 1.5 |
| $KH_2PO_4$ | 1.0 |
| $MgSO_4 \cdot 7H_2O$ | 0.5 |
| $FeSO_4 \cdot 5H_2O$ | 0.05 |
| $MnSO_4 \cdot nH_2O$* | 0.02 |
| $ZnCl_2$ | 0.001 |
| $CoCl_2$ | 0.001 |
| $CaCO_3$ | 3.0 |
| pH | 7.0 |

*: n represents an integer from 4 to 6.

TABLE 2

| Principal Medium Composition | |
|---|---|
| Component | (g/l) |
| Glucose | 75.0 |
| $KH_2PO_4$ | 1.0 |
| $MgSO_4 \cdot 7H_2O$ | 0.5 |
| Nitrogen source | 0.64 (as of N content) |

TABLE 3

| | Nitrogen Source | Amount of $CaCO_3$ Added (w/v %) | Amount of Curdlan Produced (mg/ml) |
|---|---|---|---|
| Conventional | $(NH_4)_2HPO_4$ | 0 | 0 |
| | | 0.3 | 33.4 |
| | $(NH_4)_2SO_4$ | 0 | 0 |
| | | 0.3 | 32.2 |
| | $NH_4Cl$ | 0 | 0 |
| | | 0.3 | 32.3 |
| | $(NH_2)_2CO$ | 0 | 24.9 |
| | | 0.3 | 24.6 |
| | $NaNO_3$ | 0 | 19.4 |
| | | 0.3 | 19.6 |
| Inventive | Ammonium succinate | 0 | 38.6 |
| | | 0.3 | 34.2 |

From Table 3, it is seen that the medium containing ammonium phosphate, ammonium sulfate or ammonium chloride yielded almost no curdlan in the absence of calcium carbonate, demonstrating the necessity of addition of calcium carbonate. When urea or ammonium nitrate was used, curdlan was produced but its amount was relatively small, whether calcium carbonate was added or not.

On the other hand, the medium containing ammonium succinate yielded more curdlan in the absence of calcium carbonate than in the presence thereof.

Also, the total sugar content in the culture supernatant was almost the same as the residual glucose content. This demonstrates that almost no oligomers were present in the supernatant.

EXPERIMENTAL EXAMPLE 2

Three identical solutions of 2.0 g of succinic acid in about 500 ml of tap water were prepared. These solutions were neutralized with sodium hydroxide, potassium hydroxide or calcium hydroxide, respectively (pH 7.5). After 75.0 g of glucose, 3.0 g of $(NH_4)_2HPO_4$, 1.0 g of $KH_2PO_4$, 0.5 g of $MgSO_4 \cdot 7H_2O$ and 3.0 g of $CaCO_3$ were added, each solution was diluted with water to reach a total quantity of 1 liter for a principal medium. These media were sterilized in the same manner as in Experimental Example 1.

Separately, another principal medium containing ammonium succinate as a nitrogen source was prepared in the same manner as in Experimental Example 1.

Still another principal medium was prepared in the same manner as above, but succinic acid was replaced with fumaric acid.

To each principal medium was added 2 ml of a seed culture broth of *Agrobacterium sp. biovar* I (IFO 13714) cultured in the same manner as in Experimental Example 1, followed by cultivation at 32° C. for 96 hours.

The amount of curdlan produced in the culture broth was determined in the same manner as in Experimental Example 1. The results are given in Table 4.

TABLE 4

|  | Amount of $CaCO_3$ Added (w/v %) | Amount of Curdlan Produced (mg/ml) |
|---|---|---|
| Sodium succinate | 0.3 | 32.7 |
| Potassium succinate | 0.3 | 33.5 |
| Calcium succinate | 0.3 | 32.6 |
| Ammonium succinate*[1] | 0 | 38.0 |
| Sodium fumarate | 0.3 | 32.3 |
| Potassium fumarate | 0.3 | 30.6 |
| Calcium fumarate | 0.3 | 32.6 |
| Ammonium fumarate*[2] | 0 | 37.6 |

*[1]: N content (estimated) was about 0.72 g/l.
*[2]: N content (estimated) was about 0.71 g/l.

Succinic acid and fumaric acid both offered highest curdlan production when they were used as an ammonium salt in the absence of calcium carbonate.

EXPERIMENTAL EXAMPLE 3

To the principal medium shown in Table 2, 3 ml/l of aqueous ammonia and each organic acid listed in Table 5 were added as the nitrogen sources, followed by neutralization (pH 7.5), after which each principal medium was sterilized in the same manner as in Experimental Example 1.

To each principal medium was added 2 ml of a seed culture broth of *Agrobacterium sp. biovar* I (IFO 13714) cultured in the same manner as in Experimental Example 1, followed by cultivation at 32° C. for 96 hours.

The amount of curdlan produced in the culture broth was determined in the same manner as in Experimental Example 1. The results are given in Table 5.

TABLE 5

| Organic Acid | Amount of Addition (g/l) | Amount of Curdlan Produced (mg/ml) |
|---|---|---|
| Succinic acid | 2.0 | 37.0 |
| Citric acid | 2.3 | 31.0 |
| Fumaric acid | 2.0 | 36.0 |
| Malic acid | 2.2 | 30.3 |
| α-ketoglutaric acid | 2.5 | 37.0 |
| L-lactic acid | 2.9 | 36.6 |

From Table 5, it is seen that high curdlan production is obtained when any organic acid is used. Particularly, when succinic acid, fumaric acid, α-ketoglutaric acid or L-lactic acid is used, the amount of curdlan produced is highest.

EXPERIMENTAL EXAMPLE 4

To the principal medium shown in Table 2 was added each amino acid listed in Table 6 as the nitrogen source, followed by addition of aqueous ammonia to obtain pH 7.5. The N content in each principal media was calculated as about 0.6 g/l.

Using these principal media, cultivation was conducted in accordance with Experimental Example 3, and the amount of curdlan produced was determined. The results are given in Table 6.

TABLE 6

| Amino Acid | Amount of Addition (g/l) | Amount of Curdlan Produced (mg/ml) |
|---|---|---|
| Glutamic acid | 4.0 | 36.5 |
| Aspartic acid | 4.0 | 36.3 |
| Alanine | 3.82 | 36.6 |
| Serine | 4.50 | 32.4 |
| Threonine | 5.11 | 29.7 |
| Histidine | 3.32 | 32.5 |
| Proline | 4.93 | 35.6 |

From Table 6, it is seen that particularly high curdlan production is obtained when any amino acid is used. Particularly, when glutamic acid, aspartic acid or proline is used, highest curdlan production is obtained.

EXPERIMENTAL EXAMPLE 5

A mutant of *Agrobacterium sp. biovar* I (IFO 13714) having improved capability of curdlan production was selected and named *Agrobacterium sp. biovar* I 10C3K IFO 15506. This mutant was cultured in each medium and the amount of curdlan produced was determined in the same manner as in Experimental Example 1. The results are given in Table 7.

TABLE 7

| Nitrogen Source | | Amount of $CaCO_3$ Added (w/v %) | Amount of Curdlan Produced (mg/ml) |
|---|---|---|---|
| Substance | Amount of Addition (g/l) | | |
| $(NH_4)HPO_4$ | 3.5 | 0 | 0 |
|  |  | 0.3 | 33.6 |
| $(NH_4)_2SO_4$ | 3.5 | 0 | 0 |
|  |  | 0.3 | 33.3 |
| Ammonium succinate | 2.5* | 0 | 38.9 |
|  |  | 0.3 | 35.4 |

*: 2.5 g/l of succinic acid was added.

From Table 7, it is seen that the medium containing ammonium phosphate or ammonium sulfate as a nitrogen source yields almost no curdlan in the absence of calcium carbonate, demonstrating the necessity of adding calcium carbonate. The medium containing ammonium succinate yielded more curdlan in the absence of calcium carbonate than in its presence.

EXPERIMENTAL EXAMPLE 6

*Agrobacterium sp. biovar* I 10C3K IFO 15506 was cultured and the amount of curdlan produced was determined in the same manner as in Experimental Example 3, using each organic acid listed in Table 8. The results are given in Table 8.

TABLE 8

| Organic Acid | Amount of Addition (g/l) | Amount of Curdlan Produced (mg/ml) |
| --- | --- | --- |
| Succinic acid | 2.5 | 38.9 |
| Fumaric acid | 2.5 | 37.0 |
| α-ketoglutaric acid | 2.75 | 38.3 |

From Table 8, it is seen that very high curdlan production is obtained when succinic acid, fumaric acid or α-ketoglutaric acid is used.

EXPERIMENTAL EXAMPLE 7

*Agrobacterium sp. biovar* I 10C3K IFO 15506 was cultured and the amount of curdlan produced was determined in the same manner as in Experimental Example 4, using each amino acid listed in Table 9. The results are given in Table 9.

TABLE 9

| Amino Acid | Amount of Addition (g/l) | Amount of Curdlan Produced (mg/ml) |
| --- | --- | --- |
| Glutamic acid | 4.5 | 39.0 |
| Aspartic acid | 4.5 | 37.2 |

From Table 9, it is seen that high curdlan production is obtained when glutamic acid or aspartic acid is used.

EXAMPLE 1

To 500 ml of tap water were added 1.0 g of $KH_2PO_4$ and 0.5 g of $MgSO_4 \cdot 7H_2O$, and succinic acid was added in each ratio shown in Table 10. After neutralization (pH 7.5) with aqueous ammonia, the mixture was filled up to 1 liter with tap water.

Each solution was dispensed in 200 ml conical flasks at 20 ml per flask and autoclaved at 118° C. for 15 minutes. To each flask was added a separately sterilized glucose solution to a concentration of 7.5% (w/v) to yield principal media.

To each principal medium was inoculated 2 ml of a seed culture broth of *Agrobacterium sp. biovar* I (IFO 13714) cultured in the same manner as in Experimental Example 1, followed by cultivation at 32° C. for 96 hours.

The amount of curdlan produced, curdlan yield relative to sugar and residual glucose content in the culture broth were determined in accordance with Experimental Example 1. The results are given in Table 10.

TABLE 10

| Amount of Succinic Acid Added (g/l) | Nitorogen Content* (g/ml) | Amount of Curdlan Produced (mg/ml) | Curdlan Yield Relative to Sugar (% by weight) | Residual Glucose Content (mg/ml) |
| --- | --- | --- | --- | --- |
| 1.5 | 0.46 | 28.5 | 52.0 | 20.2 |
| 2.0 | 0.61 | 35.1 | 53.5 | 9.4 |
| 2.5 | 0.76 | 38.3 | 53.3 | 3.1 |
| 3.0 | 0.91 | 38.1 | 52.0 | 1.7 |
| 4.0 | 1.21 | 35.5 | 48.0 | 1.1 |
| 6.0 | 1.82 | 31.8 | 42.4 | 0 |
| 8.0 | 2.43 | 23.7 | 31.2 | 0 |
| 10.0 | 3.03 | 12.7 | 16.9 | 0 |

*: Calculated from the amount of aqueous ammonia used for pH neutralization (estimated value).

From Table 10, it is seen that curdlan production reaches a maximum at a succinic acid concentration of 2.5 g/l, and curdlan yield relative to sugar reaching a maximum at a succinic acid concentration of 2.0 g/l.

It is also seen that the culturing speed increases as the amount of succinic acid used increases, because the residual glucose content decreases.

These findings demonstrate the feasibility of obtaining the desired curdlan yield relative to sugar, curdlan production, productivity per unit time etc. by optionally choosing the amount of succinic acid used.

Next, to about 25 ml (equivalent to 1 flask) of a culture broth containing 2.5 g/l succinic acid was added 100 ml of 1 N NaOH, followed by stirring for about 1 hour to dissolve the resulting curdlan, and subsequent centrifugation (9000 rpm, 10 minutes) for cell removal. Upon neutralization with 4 N HCl, a neutralized gel was obtained. The gel-containing solution was centrifuged, and the precipitated fraction washed with deionized water and again centrifuged (9000 rpm, 10 minutes). This procedure was conducted in two cycles for thorough desalinization, after which acetone was added, followed by vacuum drying, to yield 780 mg of purified curdlan. A 200 mg portion of this curdlan was swollen with 10 ml of deionized water, homogenized and degassed, after which it was placed in a test tube and heated at 100° C. for 10 minutes to yield a thermally coagulated gel. The gel was subjected to rheometry using a rheometer (SUN SCIENTIFIC Co., Ltd.), the gel strength being 1020 $g/cm^2$.

EXAMPLE 2

To 500 ml of tap water was added 1 g of succinic acid. After mixture neutralization with about 1.8 ml of aqueous ammonia, 10 g of glucose, 1 g of $KH_2PO_4$, 0.5 g of $MgSO_4 \cdot 7H_2O$, 0.05 g of $FeSO_4 \cdot 5H_2O$, 0.02 g of $MnSO_4 \cdot nH_2O$ (n=4–6), 0.001 g of $ZnCl_2$ and 0.001 g of $CoCl_2$ were added, followed by addition of aqueous ammonia to obtain pH 7.5, after which tap water was added to reach a final quantity of 1 liter, to yield a seed medium. This seed medium was dispensed to 200 ml conical flasks at 20 ml per flask and sterilized at 118° C. for 15 minutes. To each flask was added 1 loopful of a slant culture of *Agrobacterium sp. biovar* I (IFO 13714) or *Agrobacterium radiobacter* IFO 12607, followed by cultivation at 32° C. for 24 hours.

A principal medium was prepared by dissolving 6.25 g of succinic acid, 8.8 ml of aqueous ammonia, 2.5 g of $KH_2PO_4$ and 1.25 g of $MgSO_4 \cdot 7H_2O$ in tap water, adjusting the solution to pH 7.5 with aqueous ammonia and adding tap water to reach a total quantity of 1.8 liters. This principal medium was transferred to a 5-liter jar fermenter and sterilized at 118° C. for 15 minutes. Separately, 187.5 g of glucose was weighed and dissolved in tap water to reach a total quantity of 0.6 liters and sterilized at 121° C. for 15 minutes.

To the jar fermenter were added each of the above-described two seed culture broths (in an amount equivalent to 12 test tubes) and the above-described glucose solution, followed by cultivation (principal medium N content was 0.75 g/l) at 32° C. for 96 hours with aeration at 1 liter/min and stirring at 700 rpm. Through this operation, pH declined to 5.5 for both media, but no alkali was added. As an antifoaming agent, 0.5 ml of silicon oil (produced by Shin-Etsu Chemical Co., Ltd.) was twice added to each medium during cultivation.

The amount of curdlan produced, absolute curdlan yield and curdlan yield relative to sugar in the culture broth were determined in accordance with Experimental Example 1. The results are given in Table 11.

TABLE 11

| Strain | Amount of Curdlan Produced (mg/ml) | Absolute Curdlan Yield (g) | Curdlan Yield Relative to Sugar (% by weight) |
| --- | --- | --- | --- |
| IFO 13714 | 42.7 | 100.3 | 53.5 |
| IFO 12607 | 38.2 | 89.9 | 47.9 |

From Table 11, it is seen that both strains offer high levels of curdlan production, absolute curdlan yield and curdlan yield relative to sugar.

Using 20 ml of each of the two culture broths, purified curdlan was prepared in accordance with Example 1. Purified curdlan was obtained in amounts of 820 mg from IFO 13714 and 740 mg from IFO 12067, their gel strength being 982 g/cm$^2$ and 1005 g/cm$^2$, respectively.

EXAMPLE 3

A seed medium was prepared in accordance with Example 2, and 1 loopful of a slant culture of *Agrobacterium sp. biovar* I (IFO 13714) was added, followed by cultivation at 32° C. for 24 hours.

A principal medium was prepared in accordance with Example 2. Separately, 187.5 g of glucose was weighed and dissolved in tap water to reach a total quantity of 0.6 liters and sterilized at 121° C. for 15 minutes.

To a 5 liter jar fermenter were added the above-described seed culture broth (in an amount equivalent to 12 test tubes) and 200 ml of the above-described glucose solution, followed by cultivation under the same conditions as in Example 2.

The above-described glucose solution was added in an amount of 200 ml at 24 hours of cultivation and then 200 ml at 48 hours of cultivation. Cultivation was complete in 82 hours. Through this operation the pH of the medium decreased to 5.6, but no alkali was added.

Upon completion of cultivation, the amount of culture broth was 2.37 liters, the mount of curdlan produced was 42.3 mg/ml, the absolute curdlan yield was 100.3 g and the curdlan yield relative to sugar was about 53.5%. To the culture broth were added 5 liters of water and 10 liters of 4 N caustic soda, followed by stirring at 60° C. for 2 hours, to thoroughly dissolve the curdlan. This solution was filtered in the presence of Hyflo Super Cel as a filter aid to remove solids, and the filtrate cooled to 20° C. This filtrate was adjusted to pH 4.5 by dropwise addition of 4 N hydrochloric acid solution to yield a neutralized gel, which was separated in a continuous centrifuge to yield a precipitate fraction. This precipitate fraction was suspended in about 20 liters of tap water, centrifuged and washed. This procedure was conducted one more time, followed by dehydration with 10 liters of acetone and vacuum drying, to yield 93.5 g of purified curdlan. The gel strength of the purified curdlan, determined in accordance with Example 1, was 995 g/cm$^2$.

EXAMPLE 4

*Agrobacterium sp. biovar* I IFO 15506 and *Agrobacterium sp. biovar* I IFO 13714 were cultured in media of various succinic acid concentrations to compare their curdlan production capabilities.

Succinic acid, weighed in an amount of 6.25 g, 7.50 g or 8.75 g, was dissolved in tap water. After each solution was neutralized with 8.8 ml, 10.5 ml or 12.2 ml, respectively, of aqueous ammonia, 2.5 g of $KH_2PO_4$, 1.25 g of $MgSO_4 \cdot 7H_2O$, 25 mg of $FeSO_4 \cdot 7H_2O$, 50 mg of $CaCl_2 \cdot 2H_2O$, 0.25 mg of $CoCl_2$, 0.25 mg of $ZnCl_2$, 0.25 mg of $CuSO_4 \cdot 5H_2O$ and 1 ml of silicon oil (produced by Shin-Etsu Chemical Co., Ltd.) were sequentially added in that order, followed by aqueous ammonia adjustment to obtain pH 7.5, and water was added to reach a final quantity of 1.8 liters. Each was transferred to a jar fermenter and sterilized at 121° C. for 20 minutes to yield a principal medium. Separately, 225 g of glucose was weighed and diluted with tap water to reach a final quantity of 0.6 liters and sterilized at 121° C. for 15 minutes.

*Agrobacterium sp. biovar* I IFO 15506 and *Agrobacterium sp. biovar* I IFO 13714 were seed cultured in accordance with the method of Example 2. A 240 ml portion of each seed culture broth and 300 ml of the above-described sterile glucose solution were added to the above-mentioned jar fermenter, followed by cultivation at 32° C. with aeration at 1 liter/min and stirring at 800 rpm. An additional 300 ml of the sterile glucose solution was added at 24 hours of cultivation, and cultivation was continued for a total of 96 hours. The succinic acid concentrations in the media were about 2.5, 3.0 and 3.5 g/l, respectively.

The amount of curdlan produced, absolute curdlan yield and residual glucose content in each culture broth were determined in accordance with Experimental Example 1. The results are given in Table 12.

TABLE 12

| Strain | Amount of Succinic Acid Added (g/l) | Cultivation Time | Amount of Curdlan Produced (mg/ml) | Absolute Curdlan Yield (g) | Residual Glucose Content (mg/ml) |
| --- | --- | --- | --- | --- | --- |
| IFO 15506 | 2.5 | 96 | 40.2 | 95.3 | 18.4 |
|  | 3.0 | 96 | 44.6 | 104.8 | 9.8 |
|  | 3.5 | 84 | 49.6 | 116.1 | 0 |
| IFO 13714 | 2.5 | 96 | 38.2 | 90.5 | 21.6 |
|  | 3.0 | 96 | 42.7 | 100.3 | 12.3 |
|  | 3.5 | 96 | 46.8 | 109.7 | 2.5 |

From Table 12, it is seen that when *Agrobacterium sp. biovar* I IFO 15506 was used, cultivation time shortened and curdlan production speed increased as the amount of succinic acid added increased. Similarly, when *Agrobacterium sp. biovar* I IFO 13714 was used, curdlan production speed increased as the amount of succinic acid added increased.

What is claimed is:

1. A method for producing curdlan using no inorganic salt as a nitrogen source, which comprises:

culturing a microbe belonging to the genus Agrobacterium or Alcaligenes in a medium comprising a nitrogen source consisting essentially of an ammonium salt of an organic carboxylic acid which the microbe can assimilate, wherein the curdlan is produced and accumulated, and wherein the organic carboxylic acid is (a) an organic carboxylic acid selected from the group consisting of succinic acid, fumaric acid, α-ketoglutaric acid and lactic acid, or (b) an amino acid selected from the group consisting of glutamic acid, aspartic acid, alanine, proline, serine, threonine and histidine, and then harvesting the curdlan.

2. The method of claim 1, wherein the organic carboxylic acid is succinic acid.

3. The method of claim 1, wherein the amount of the organic carboxylic acid is about 0.5 to about 20 g/l in the medium.

4. The method of claim 1, wherein the medium contains a total nitrogen content of about 0.4 to about 3 g/l.

5. A method for producing curdlan using no inorganic salt as a nitrogen source, which comprises:

culturing a microbe belonging to the genus Agrobacterium or Alcaligenes in a medium comprising a nitrogen source consisting essentially of an ammonium salt of an organic carboxylic acid which the microbe can assimilate, wherein the curdlan is produced and accumulated, wherein the amount of the organic carboxylic acid is about 0.5 to about 20 g/l, and wherein the organic carboxylic acid is selected from the group consisting of succinic acid, fumaric acid, α-ketoglutaric acid and lactic acid, and then harvesting the curdlan.

6. A method for producing curdlan using no inorganic salt as a nitrogen source, which comprises:

culturing a microbe belonging to the genus Agrobacterium or Alcaligenes in a medium comprising a nitrogen source consisting essentially of an ammonium salt of an organic carboxylic acid which the microbe can assimilate, wherein the curdlan is produced and accumulated, wherein the amount of the organic carboxylic acid is about 0.5 to about 20 g/l, and wherein the organic carboxylic acid is selected from the group consisting of glutamic acid, aspartic acid, alanine, proline, serine, threonine and histidine, and then harvesting the curdlan.

7. A method for producing curdlan using no inorganic salt as a nitrogen source, which comprises:

culturing a microbe belonging to the genus Agrobacterium or Alcaligenes in a medium comprising a nitrogen source consisting essentially of aqueous ammonia and an organic carboxylic acid which the microbe can assimilate, the medium being prepared by separately adding the aqueous ammonia and the organic carboxylic acid to the medium, which aqueous ammonia and organic carboxylic acid may form an ammonium salt of the organic carboxylic acid in the medium, wherein the curdlan is produced and accumulated, and wherein the organic carboxylic acid is (a) an organic carboxylic acid selected from the group consisting of succinic acid, fumaric acid, α-ketoglutaric acid and lactic acid, or (b) an amino acid selected from the group consisting of glutamic acid, aspartic acid, alanine, proline, serine, threonine and histidine, and then harvesting the curdlan.

8. The method of claim 7, wherein the organic carboxylic acid is succinic acid.

9. The method of claim 7, wherein the amount of the organic carboxylic acid is about 0.5 to about 20 g/l in the medium.

10. The method of claim 7, wherein the medium contains a total nitrogen content of about 0.4 to about 3 g/l.

* * * * *